(12) United States Patent
Ortais et al.

(10) Patent No.: US 11,654,410 B2
(45) Date of Patent: May 23, 2023

(54) METHOD FOR PREPARING BIODEGRADABLE MICROCAPSULES AND MICROCAPSULES THUS OBTAINED

(71) Applicants: GEM INNOV, Gemenos (FR); UNIVERSITÉ D'AIX MARSEILLE, Marseilles (FR); CENTRE NATIONAL DE LA RECHERCHE SCIENTIFIQUE, Paris (FR)

(72) Inventors: Yves Ortais, Gemenos (FR); Thierry Ribeiro, La Fare les Oliviers (FR); Kaouthar Oudoua, Marseilles (FR); The Hien Ho, Marseilles (FR); Didier Gigmes, Allauch (FR); Catherine Guillaneuf, Marseilles (FR); Yohann Guillaneuf, Marseilles (FR)

(73) Assignee: GEM INNOV, Gemenos (FR)

( * ) Notice: Subject to any disclaimer, the term of this patent is extended or adjusted under 35 U.S.C. 154(b) by 88 days.

(21) Appl. No.: 16/876,006

(22) Filed: May 16, 2020

(65) Prior Publication Data

US 2020/0360889 A1  Nov. 19, 2020

Related U.S. Application Data

(60) Provisional application No. 62/927,622, filed on Oct. 29, 2019.

(30) Foreign Application Priority Data

May 16, 2019 (FR) ...................................... 1905127
Oct. 29, 2019 (FR) ...................................... 1912148

(51) Int. Cl.
*B01J 13/16* (2006.01)
*C08F 220/34* (2006.01)
(Continued)

(52) U.S. Cl.
CPC .............. *B01J 13/16* (2013.01); *B01J 13/22* (2013.01); *C08F 220/34* (2013.01); *C08G 73/02* (2013.01);
(Continued)

(58) Field of Classification Search
None
See application file for complete search history.

(56) References Cited

U.S. PATENT DOCUMENTS 6,569,528 B2  5/2003  Nam et al.
6,998,115 B2 *  2/2006  Langer ................ A61K 31/713
424/78.37
(Continued)

FOREIGN PATENT DOCUMENTS

CN  103230766 B  12/2014
CN  105646911 A  6/2016
(Continued)

OTHER PUBLICATIONS

Maurya et al. A Review on Acrylate Terminated Urethane Oligomers and Polymers: Synthesis and Applications, Polymer-Plastics Technology and Engineering, 57, 7, 625-656 (2018).
(Continued)

*Primary Examiner* — Jeffrey D Washville
(74) *Attorney, Agent, or Firm* — Ladas & Parry LLP; Malcolm J. MacDonald, Esq.

(57) ABSTRACT

A method for manufacturing microcapsules containing an active substance, the method including: providing an aqueous solution of a surfactant, an oily phase comprising the active substance and a first monomer, and a polar phase comprising a second monomer; preparing an oil-in-water emulsion by adding the oily phase to the aqueous solution of the surfactant; adding the polar phase to the oil-in-water emulsion, in order to obtain a polymer in a reaction mixture,
(Continued)

by polymerization of the first monomer and the second monomer; isolating the microcapsules, including a wall formed by the polymer and containing the active substance, from the reaction mixture; wherein the polymer is a poly (beta-amino ester). Microcapsules obtained by the method.

14 Claims, 10 Drawing Sheets

(51) Int. Cl.
| | | |
|---|---|---|
| B01J 13/22 | (2006.01) | |
| C08G 73/02 | (2006.01) | |
| C08L 77/06 | (2006.01) | |
| C09D 101/02 | (2006.01) | |

(52) U.S. Cl.
CPC .......... *C08L 77/06* (2013.01); *C08G 2230/00* (2013.01); *C08L 2201/06* (2013.01); *C09D 101/02* (2013.01)

(56) References Cited

U.S. PATENT DOCUMENTS

| | | | |
|---|---|---|---|
| 7,119,057 | B2 | 10/2006 | Popplewell et al. |
| 7,294,612 | B2 | 11/2007 | Popplewell et al. |
| 7,427,394 | B2 | 9/2008 | Anderson et al. |
| 7,585,824 | B2 | 9/2009 | Popplewell et al. |
| 7,736,695 | B2 | 6/2010 | Schwantes et al. |
| 7,799,752 | B2 | 9/2010 | Ness et al. |
| 7,803,422 | B2 | 9/2010 | Schwantes et al. |
| 7,985,445 | B2 | 7/2011 | Schwantes et al. |
| 8,071,082 | B2 | 12/2011 | Zugates et al. |
| 8,168,225 | B2 | 5/2012 | Casan Giner et al. |
| RE43,612 | E | 8/2012 | Anderson et al. |
| 8,287,849 | B2 | 10/2012 | Langer et al. |
| 8,455,098 | B2 | 6/2013 | Schwantes |
| 8,557,231 | B2 | 10/2013 | Langer |
| 8,562,966 | B2 | 10/2013 | Zugates et al. |
| 8,685,446 | B2 | 4/2014 | Casana Giner et al. |
| 8,715,544 | B2 | 5/2014 | Schwantes |
| 8,877,217 | B2 | 11/2014 | Kim et al. |
| 8,911,783 | B2 | 12/2014 | Casana Giner et al. |
| 9,079,152 | B2 | 7/2015 | Markus et al. |
| 9,101,143 | B2 | 8/2015 | Markus et al. |
| 9,101,666 | B2 | 8/2015 | Langer et al. |
| 9,192,908 | B2 | 11/2015 | Schwantes |
| 9,272,043 | B2 | 3/2016 | Saltzman et al. |
| 9,567,430 | B2 | 2/2017 | Saltzman et al. |
| 9,687,569 | B2 | 6/2017 | Zhang et al. |
| 9,700,627 | B2 | 7/2017 | Langer et al. |
| 9,895,451 | B2 | 2/2018 | Saltzman et al. |
| 9,944,886 | B2 | 4/2018 | Hitchcock |
| 9,944,887 | B2 | 4/2018 | Tasker et al. |
| 9,951,293 | B2 | 4/2018 | Hitchcock et al. |
| 9,951,294 | B2 | 4/2018 | Hitchcock et al. |
| 9,962,321 | B2 | 5/2018 | Baxter et al. |
| 10,335,500 | B2 | 7/2019 | Hanes et al. |
| 10,465,042 | B2 | 11/2019 | Cui et al. |
| 10,682,422 | B2 | 6/2020 | Saltzman et al. |
| 2005/0043209 | A1 | 2/2005 | Schmiedel et al. |
| 2005/0244504 | A1 | 11/2005 | Little |
| 2010/0086603 | A1 | 4/2010 | Shirley et al. |
| 2011/0020648 | A1 | 1/2011 | Fukazawa et al. |
| 2011/0045473 | A1* | 2/2011 | De Fougerolles .... C12N 15/111 435/23 |
| 2011/0057340 | A1 | 3/2011 | Perichaud |
| 2011/0268778 | A1 | 11/2011 | Dihora et al. |
| 2011/0269657 | A1 | 11/2011 | Dihora et al. |
| 2014/0037703 | A1 | 2/2014 | Dihora et al. |
| 2016/0184196 | A1 | 6/2016 | Baxter |
| 2017/0283830 | A1 | 10/2017 | Saltzman |
| 2018/0000968 | A1 | 1/2018 | Oh et al. |
| 2018/0078468 | A1 | 3/2018 | Jerri |
| 2018/0360706 | A1 | 12/2018 | Dihora et al. |
| 2019/0134592 | A1 | 5/2019 | Rost et al. |
| 2019/0194444 | A1 | 6/2019 | Capasso Palmiero et al. |
| 2019/0224638 | A1 | 7/2019 | Schwantes |
| 2019/0275490 | A1 | 9/2019 | Bachawala |
| 2020/0113821 | A1 | 4/2020 | Saltzman |
| 2020/0122110 | A1 | 4/2020 | Zhang et al. |
| 2020/0123219 | A1 | 4/2020 | Hutchinson |
| 2020/0129947 | A1 | 4/2020 | Ouali et al. |
| 2020/0164332 | A1 | 5/2020 | Demoulin |
| 2020/0172663 | A1 | 6/2020 | Katzmarek |

FOREIGN PATENT DOCUMENTS

| | | |
|---|---|---|
| CN | 110559448 A | 12/2019 |
| EP | 1084860 A2 | 3/2001 |
| EP | 1928594 B1 | 1/2015 |
| EP | 2913103 A1 | 9/2015 |
| EP | 1991052 B1 | 9/2017 |
| EP | 2994318 B1 | 7/2019 |
| JP | 4200764 B2 | 12/2008 |
| WO | 03/016369 A1 | 2/2003 |
| WO | 2007/070118 A1 | 6/2007 |
| WO | 2009/115671 A1 | 9/2009 |
| WO | 2013/114025 A1 | 8/2013 |
| WO | 2019121736 A1 | 6/2019 |
| WO | 2019121738 A1 | 6/2019 |
| WO | 2020009439 A1 | 1/2020 |

OTHER PUBLICATIONS

Hodnett et al. Journal of Polymer Science: A Study of the Mechanism of Interfacial Polyamidation and Polyesterification, vol. 58, pp. 1415-1421 (1962).
Brey et al. Elsevier—Controlling poly(b-amino ester) network properties throughmacromer branching, Acta Biomaterialia 4 (2008) 207-217.
Brey et al.—Influence of macromer molecular weight and chemistry on poly(b-amino ester) network properties and initial cell interactions—Department of Bioengineering, University of Pennsylvania (2007).
Lynn et al.—J. Am. Chem. Soc.—Degradable Poly(â-amino esters): Synthesis, Characterization, and Self-Assembly with Plasmid DNA (2000).
Roux et al.—ACS Macro Letters—Facile and Rapid Access to Glyconanocapsules by CuAAC Interfacial Polyaddition in Miniemulsion Conditions (2012).
Liao et al.—Journal of Applied Polymer Science—Fragrance-containing microcapsules based on interfacial thiol-ene polymerization (2016).
Amato et al.—ACS Applied Materials and Interfaces—Functional Microcapsules via Thiol-Ene Photopolymerization in Droplet-Based Microfluidics (2020).
Morgan et al.—Journal of Polymer Science—Interfacial Polycondensation. 11. Fundamentals of Polymer Formation at Liquid Interfaces—vol. XL, pp. 299-327 (1959).
Eareckson, III—Journal of Polymer Science—Interfacial Polycondensation—vol. XL, pp. 399-406 (1959).
Cheng et al.—Bio Macromolecules—Michael Addition Polymerization of Trifunctional Amine and Acrylic Monomer: A Versatile Platform for Development of Biomaterials (2016).
Li et al. Elsevier—Int. Journal of Pharmaceutics—Microencapsulation by solvent evaporation: State of the art for process engineering approaches (2008).
Liu et al.—Advanced Healthcare Materials—Poly(β-Amino Esters): Synthesis, Formulations, and Their Biomedical Applications (2019).
Little et al.—MIT—Poly-β amino ester-containing microparticles enhance the activity of nonviral genetic vaccines (2004).
Wu et al.—Polymers for Advanced Technologies—Preparation of biodegradable microcapsules through an organic solvent-free interfacial polymerization method (2018).
Safranski et al.—Elsevier—The effect of chemistry on the polymerization, thermo-mechanical properties and degradation rate of poly(β-amino ester) networks (2010).

(56) References Cited

OTHER PUBLICATIONS

Siebert et al.—Chem. Comm.—Towards copper-free nanocapsules obtained by orthogonal interfacial "click" polymerization in miniemulsion (2012).

* cited by examiner a)

b)

METHOD FOR PREPARING BIODEGRADABLE MICROCAPSULES AND MICROCAPSULES THUS OBTAINED

This application claims priority to French Patent Application No. 1905127, filed May 16, 2019; French Patent Application No. 1912148, filed Oct. 29, 2019; and U.S. Provisional Patent Application No. 62/927,622, filed Oct. 29, 2019; all of which are incorporated herein by reference.

BACKGROUND OF THE INVENTION

Field of the Invention

The invention relates to the field of microcapsules, and more particularly the methods for manufacturing microcapsules for the purpose of containing active substances, such as essential oils. More particularly, the invention related to a method for preparing biodegradable microcapsules. This method proceeds via interfacial polymerization of multifunctional compounds, leading to poly(beta-amino ester)s. The invention also relates to the biodegradable microcapsules obtained by this method.

Description of Related Art

Microencapsulation is a method that makes it possible to protect a reactive, sensitive, or volatile substance (hereinafter referred to "active principle") in a capsule of which the size can vary from the nanometer to the micrometer. The core of the capsule is therefore isolated from the outside environment by a wall (also called "shell"). This makes it possible to delay the evaporation, release, or deterioration thereof; there are many applications that make use of these technical effects when the microcapsules are incorporated into a complex formulation or applied on a product.

By way of example, microcapsules can be used to distribute, in a controlled manner, the active principle that they contain, which can, in particular, be a biocidally active substance, an insecticide, a disinfectant, or a fragrance; this can be done by diffusion through the wall, or under the influence of an external force that breaks the wall. In certain applications, the release of the active principle is done under the influence of an external force that breaks the wall of the microcapsules; thus a glue can be released (see, for example, WO 03/016369—Henkel), or a reagent (see, for example, WO 2009/115671—Catalysis).

In other applications, the content of the microcapsule cannot escape, but the change in color thereof, under the effect of a variation in temperature (thermochromism) or irradiation UV (photochromism), is visible from the outside (see, for example, WO 2013/114 025—Gem Innov, or WO 2007/070118—Kimberly-Clark, or EP 1 084 860 The Pilot Ink Co.).

There are several techniques for preparing microcapsules. The main ones are spray-drying, interfacial polymerization, solvent evaporation, self-assembly of polymers by the Layer by Layer (LbL) technique, and the preparation of colloidosomes. All of these techniques make it possible to obtain stable microcapsules of an average diameter of 10 μm. Interfacial polymerization is, however, the preponderant technique, because it allows for rapid preparation, and in a single step, of microcapsules, of which the wall is sufficiently solid for the latter to be isolated, and, thus, be used in many applications.

The formation of microcapsules by interfacial polymerization is usually done in 4 steps: (i) preparing a first phase containing the active principle (for example an essential oil) and an organosoluble monomer; (ii) forming an emulsion by first phase dispersion in an aquatic environment that contains the surfactant, and which represents the second phase; (iii) adding the water soluble monomer in the second phase; and (iv) forming and maturing of the membrane by reaction of the monomers by polycondensation at the interface.

Several families of polymer are conventionally used to manufacture the wall of microcapsules (Perignon, C. et al., *Journal of Microencapsulation* 2015, 32 (1), 1-15), such as polyamides (PA), polyurethanes (PU) or polyureas. The elaboration of walls of microcapsules from PA in general uses monomers of the diamine type (hexamethylene diamine for example) and acyl chloride (sebacoyl chloride for example), while those made from PU make use of monomers of the di-isocyanate type (HDI, IPDI etc.) and diols. In the case of polyureas, monomers are used of the di-isocyanate and diamine type, or di-isocyanates alone, of which the hydrolysis at the interface produces the amines that allow for the synthesis of the urea function. By way of example, aforementioned document WO 2009/115671 describes the formation of microcapsule walls by interfacial polycondensation, from different mixtures of monomers: hexamethylene diisocyanate (HMDI) and ethylene diamine; tetraethylorthosilicate (TEO) and 3-(trimethoxysilyl)propylmethacrylate (MPTS); 2,4-tolylenediisocyanate (TDI) and 1,3 phenylenediamine; 2,4-toluene diisocyanate and 1,3-phenylene diamine.

Some work already exists relating to the preparation of microcapsules by interfacial polymerization, using other types of polymers. Mention can be made for example of the work of J. Bernard on the preparation of glyconanocapsules by azide—alkyne cycloaddition catalyzed by copper (R. Roux et al., *J. ACS Macro Lett.* 2012, 1 (8), 1074-1078), or the work of K. Landfester (Siebert et al., *Chem. Commun.* 2012, 48, 5470-5472), or that of L. Shi et al. (*J. Appl. Polym. Sci.* 2016, 133 (36), 168-7) as well as D. Patton et al. (*ACS Appl. Mater. Interfaces,* 2017, 9 (4), 3288-3293), who were also able to prepare microcapsules by thiol-ene chemistry, initiated by, respectively, a base and a photoinitiator.

A rather wide spectrum of polymeric materials is, therefore, available to those skilled in the art to select the type of microcapsule suitable for a given use. Thus, microcapsules are already used in many technical applications, but their application potential has not yet been fully recognized, and this is a highly-emerging sector destined to increase substantially from the moment when the wall of microcapsules responds to increasingly stringent criteria in terms of toxicity and recyclability.

However, microcapsules represent microparticles of polymeric materials. For several years now, microparticles of polymeric materials have been identified as an area of ecological concern, due to the wide dissemination thereof in the ecosystems, in the ground, in aquatic and maritime ecosystems, to locations far from where they were introduced into the ecosystem. This wide dissemination is detrimental not only, generally, for the organisms present in these ecosystems, but could also have harmful consequences on human health. Increasingly stringent regulations have already been announced, which restrict the use of plastic materials that can form microparticles during the degradation thereof, in a situation in a natural environment, and, a fortiori, of plastic materials used straightaway in the form of microparticles.

For ecological reasons, it can appear as a contradiction to seek to develop a new product consisting of polymeric microparticles. It has consequently appeared to be desirable to have microcapsules made from a degradable polymeric material. It must be noted that the microcapsules used in many special applications, and which can be incorporated into many products in common use (such as, textile materials, cosmetic, or phyto-sanitary products), or for technical use (such as, paints, varnishes, or inks), will not normally be collected at end-of-life, and therefore cannot be the object of a biodegradation by composting, such as can be considered for plastic products that are collected. Thus, the degradability of the plastic materials that form the wall of microcapsules cannot be based on the chemical mechanisms that take place during composting. In this context, the question of knowing whether or not the degradability of the microcapsules entails a biological mechanism is rather unimportant; what is important is the degradability thereof in an ecosystem, regardless of the chemical mechanism of this degradation. By way of example, a fermentation would be a biodegradation, while a simple degradation in an ecosystem under the effect of light could be an independent photochemical reaction of the ecosystem; in reality, the situation will often be mixed, especially if the degradation unfolds in steps. In what follows, the expression "(bio)degradable" will be used to designate the characteristic of a material to be degraded in a natural environment over a rather short scale of time (weeks, or a year), according to the characteristics of this natural environment and of the exposure of the material to the various agents present in this natural environment.

It is observed that all the previously developed microcapsules lead to preparation of polymer chains (polyamide, polyurea, polyurethane, etc.) which will either be physically entangled in the case of a reaction between bifunctional compounds, or then crosslinked in the case of one or more multifunctional compounds (functionality 3). In any case, the walls are not (bio)degradable due to the nature of the polymer chain.

The problem that this invention seeks to resolve is to present a new type of microcapsules, which are easy to synthesize, without calling upon toxic and/or expensive raw materials, which are (bio)degradable in the natural environment, which can be used with a large number of active principles, and which provide good external protection to the active principle that it is intended to contain.

SUMMARY OF THE INVENTION

During their research work, the inventors found that a possibility for obtaining degradable microcapsules would be to prepare walls made from polyester, which is a polymer known for the (bio)degradability thereof. Literature shows that studies have already been conducted on this theme, and it has been shown that the reaction speed between acid chlorides and diols was very slow. This system is thus not very suitable for interfacial polymerization (see E. M. Hodnett and D. A. Holmer, *J Polym Sci*, 1962, 58, 1415-21). Particular conditions such as the use of bisphenol A as a diol and/or a reaction at a very high pH has made it possible to obtain microcapsules (see W. Eareckson, *J. Polym. Sci*, 1959, 399-406; see also P. W. Morgan and S. L. Kwolek, *J Polym Sci*, 1959, 299-327) but these conditions are too constraining for many internal phases and/or applications. In addition the slowness of the polymerization reactions is detrimental to the use thereof industrially in economic terms and in terms of short or even continuous production cycles. Thus, the inventors did not continue down this path.

According to the invention, the problem is resolved by using microcapsules made from poly(beta-amino)ester (abbreviated here as PBAE). According to the invention, these microcapsules are synthesized in a single reaction step by an addition reaction of amine functions on acrylate functions (reaction known as "Michael addition"), by interfacial polymerization. This reaction leads to the micro-encapsulation of the organic phase without forming by-products (see the reaction scheme in FIG. 6). The presence of ester functions in the backbone of the PBAE gives the polymer good degradation properties by hydrolysis.

Poly(beta-amino ester)s are known as such and have been used extensively in the last few years (Lynn, D. M.; Langer, R. *J. Am. Chem. Soc.* 2000, 122 (44), 10761-10768.; Liu, Y.; Li, Y.; Keskin, D.; Shi, L. *Adv. Healthcare Mater.* 2018, 2 (2), 1801359-24) thanks to the biocompatibility and biodegradability properties thereof, and today they represent a family of materials that has many applications such as biomaterials (for example as a vector for anti-cancer molecules, as an antimicrobial material, and for tissue engineering.)

The application fields of poly(beta-amino ester)s are very vast (see FIG. 9).

Generally, it is known that reactions of the aza-Michael addition type can be carried out in a wide range of solvents ranging from halogenated apolar solvents (dichloromethane or chloroform for example) to polar solvents such as dimethylsulfoxide (DMSO) for example (Liu, Y.; Li, Y.; Keskin, D.; Shi, L. *Adv. Healthcare Mater.* 2018, 2 (2), 1801359-24). In practice, PBAEs are substantially prepared in a solution and are then formulated to produce for example micelles, particles, gel/hydrogels, or films (the so-called Layer by Layer technique). Oligo-PBAEs have also been crosslinked in a second step either by photopolymerization (Brey, D. M.; Erickson, I.; Burdick, J. A. *J. Biomed. Mater. Res.* 2008, 85A (3), 731-741.7), or in the presence of di-isocyanates.

It is also known that linear or crosslinked PBAEs are relatively stable in a medium at neutral pH but degrade more quickly by hydrolysis of the ester functions at an acidic or basic pH. This hydrolysis phenomenon leads to the release of small molecules such as bis(β-amino acid)s and diols when linear PBAEs are used; these molecules are known to be non-toxic with regards to mammalian cells, and of low influence on the metabolism of healthy cells.

According to a substantial characteristic of the present invention microcapsules that have a wall made from PBAE are synthesized by interfacial polymerization.

More precisely, according to the invention the problem is resolved by a method wherein the Michael polycondensation reaction between amine functions and acrylate functions is used to obtain Poly(Beta-Amino Esters) (PBAE) by interfacial polymerization. The inventors found that this method, which can be applied to different active principles to be encapsulated, makes it possible to prepare stable microcapsules that can be isolated by drying and which have the property of being (bio)degradable.

The method of microencapsulation according to the invention comprises the following steps:

(a) Dispersing one or of more compounds that have at least two acrylate functions in an organic solution (also called "oily phase" in the context of an emulsion) forming the phase to be encapsulated (and comprising, where applicable, the active principle);

(b) Adding an excess in relation to the preceding volume of an aqueous phase comprising one or more surfactants, followed by an emulsification;

(c) Adding to the emulsion obtained in step (b) of one or of more compounds including at least one primary amine function and/or two secondary amine functions and polymerization reaction at a temperature comprised between about 20° C. and 100° C.;

(d) Collecting, washing and drying the microcapsules.

Thus, a first object of the invention is a method for manufacturing microcapsules containing a so-called active substance, method wherein:

An aqueous solution of a surfactant, an oily phase comprising said active substance and at least one first monomer X, and a polar phase comprising at least one second monomer Y is provided;

An emulsion of the O/W type is prepared by adding said oily phase to said aqueous solution of the surfactant;

Said polar phase is added to said O/W emulsion, in order to allow for the obtaining of a polymer by polymerization of said monomers X and Y;

From this reaction mixture said microcapsules including a wall formed by said polymer and containing said active substance are isolated;

said method being characterized in that said polymer is a poly(beta-amino ester).

Said first monomer X is selected from (multi)acrylates, in particular (multi)acrylates of formula X'—(—O(C=O)—CH=CH$_2$)$_n$ with n≥2 and where X' represents a molecule whereon n acrylate units are grafted.

Said first monomer X is, preferably, selected from (multi) acrylates of formula X'—(—O(C=O)—CH=CH$_2$)$_n$ with n≥4 and where X' represents a molecule whereon n acrylate units are grafted. More precisely, it is advantageously selected from the group formed by:

diacrylates, and more preferably those described in the article of Nayak et al. (*Polymer-Plastics Technology and Engineering*, 2018, 57, 7, 625-656);

triacrylates, in particular C$_{15}$O$_6$H$_{20}$ (CAS no. 15625-89-5, i.e. trimethylol propane triacrylate), tetraacrylates, pentaacrylates, hexaacrylates, mixtures between these different acrylates of the type O[CH$_2$C(CH$_2$OR)$_3$]$_2$ where R is H or COCH=CH$_2$; -(multi)acrylates described in the article of Nayak et al. (*Polymer-Plastics Technology and Engineering*, 2018, 57, 7, 625-656);

polymers carrying acrylic pendant functions;

functional PBAE oligos, prepared for example by reaction of diacrylate compounds with a functional primary amine and/or a functional secondary diamine;

the mixture of different compounds described hereinabove.

Said second monomer Y is selected from amines. More precisely, it is advantageously selected from the group formed by:

primary amines R—NH$_2$;

primary diamines of the type NH$_2$(CH$_2$)$_n$NH$_2$ where n is an integer that can typically be comprised between 1 and 20, and which is preferably 2 or 6;

secondary diamines comprising an aromatic center such as meta-xylylene-diamine;

primary (multi)amines such as tris(2-aminoethyl)amine;

secondary diamines such as piperazine;

(multi)amines comprising primary and secondary amine functions, such as tetraethylene pentamine;

polymers having primary and or secondary amine functions such as polyethyleneimine.

In an embodiment said polymerization of said monomers is done under stirring at a temperature comprised between 20° C. and 100° C., and preferably between 30° C. and 90° C.

Another object of the invention is a microcapsule containing a so-called active substance, characterized in that the wall thereof is formed of poly(beta-amino ester).

Yet another object of the invention is a microcapsule that can be obtained by the method according to the invention.

The shell of the microcapsules prepared by this method can be further modified by adding a polymeric coating that is deposited onto the surface of the microcapsules.

Said deposition can be carried out by adding a polymer dispersed in an aqueous phase which will form a coating on the surface of the microcapsules. Polysaccharides (such as cellulose, starch, alginates, chitosan) and their derivatives can be used for example as polymers.

Another possibility for modifying the shell of the microcapsules is to add a radical initiator either to the aqueous phase or to the organic phase. Another possibility is to react the residual amine functions on the surface with water soluble monofunctional acrylates in order to modify the surface state of the microcapsules.

DETAILED DESCRIPTION OF THE INVENTION

In the following detailed description, embodiments of the present description, many specific details are disclosed in order to provide a more in-depth understanding of the present invention and in order to allow those skilled in the art to execute the invention. However, it will appear to those skilled in the art that the present description can be implemented without these specific details. In other cases, well-known characteristics were not described in detail in order to avoid unnecessarily overloading the description.

FIGS. 1 to 18 show certain aspects of the invention, but do not limit the scope thereof.

Figure 7:
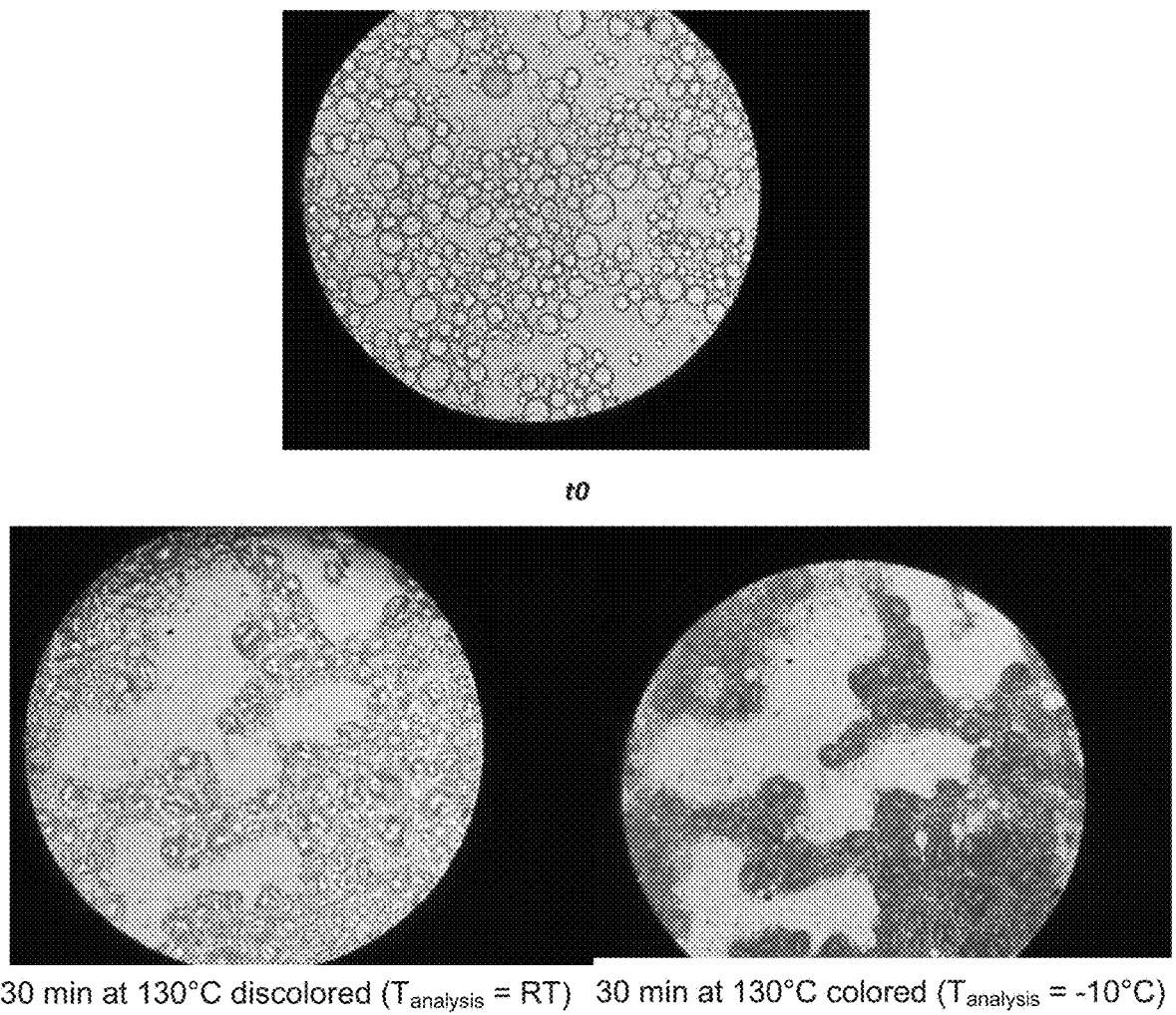
FIG. 7 shows that the thermochromic microcapsules are stable after passing in an oven for 30 min and that the thermochromic function thereof is retained.
Figure 17:
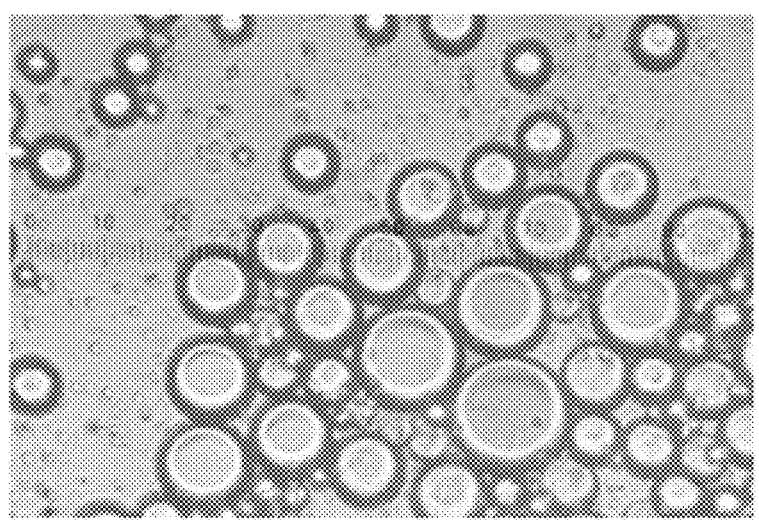
FIG. 17 shows a photograph of microcapsules according to yet another example of the invention.
Figure 18:
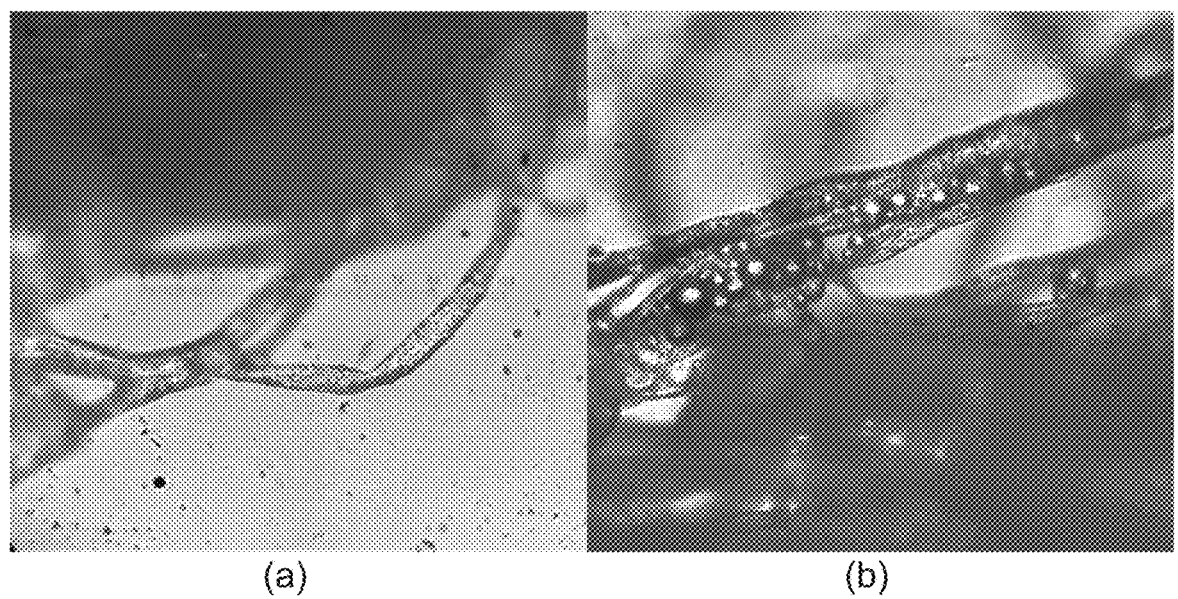
FIG. 18 shows a photograph of a cotton fiber which has been put in contact with microcapsules according to the invention, the surface of which has been modified (picture (b)), or not modified (picture (a)).

FIGS. 2 to 5 relate to Example 1. FIG. 7 relates to Example 2, FIG. 8 to Example 3, FIG. 8 to Example 3, FIG. 10 to Example 6, FIG. 11 to Example 7, FIG. 12 to Example 10, FIG. 13 to Example 11, FIG. 14 to Example 13; FIG. 15 to Example 14, FIG. 16 to Example 15, FIG. 17 to Example 17, and FIG. 18 to Example 18. FIGS. 2 to 5 and 10 to 14 are optical micrographs; the horizontal bar at the bottom left of the image represents a length of 50 μm. FIGS. 17 and 18 are also optical micrographs.

Figure 1:
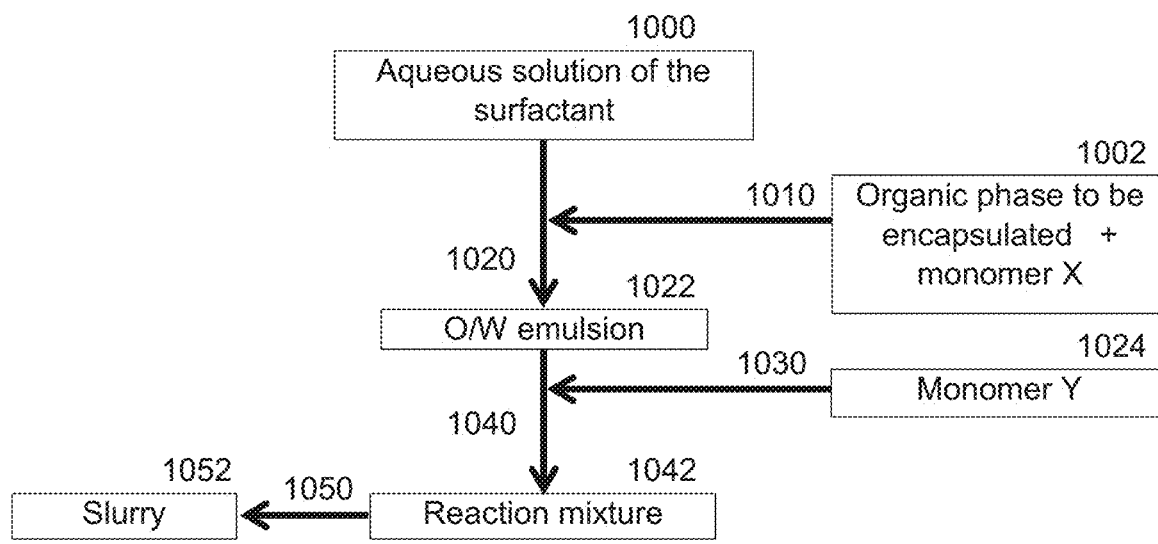
FIG. 1 shows the general diagram of the method according to the invention. The four-digit numerical marks designate steps of this method.

FIG. 1 shows a general diagram of the method according to the invention. The aqueous solution of surfactant (1000) is prepared. An organic solution (also called "oily phase") is also prepared, comprising the phase to be encapsulated (which comprises the so-called active substance) and the monomer X (1002). In step 1010, this oily phase 1002, which is an organic solution, is added to said aqueous solution 1000, and in step 1020 an emulsion 1022 of the O/W (oil-in-water type, according to a designation known to those skilled in the art), is obtained. In this emulsion, said organic phase is the so-called oily phase (O phase). In step 1030, to said emulsion 1022 is added an aqueous solution of the monomer Y 1024. In step 1040, the polymerization reaction leads to a reaction mixture 1042, from which is then formed, in step 1050, a heterogeneous mixture 1052, called a slurry, that comprises, in suspension with an aqueous base, the microcapsules that contain the phase to be encapsulated.

Step 1050, as a general rule, involves a temperature of the reaction mixture 1042 greater than about 20° C., typically comprised between 20° C. and 100° C. A temperature comprised between about 30° C. and about 90° C. is preferred, and even more preferably between about 40° C. and about 80° C.

This method can be applied to different monomers X and Y. According to the invention, the monomer X is a (multi) acrylate, and the monomer Y is an amine, preferably, a primary amine, and/or a primary (multi)amine, and/or a secondary diamine, and/or a compounds having primary and secondary amines.

"(Multi)acrylate" is defined as any compound of formula X'—(—O(C=O)—CH=CH$_2$)$_n$, where n≥2, and where X' represents a molecule whereon n acrylate units are grafted.

"Primary (multi)amine" is defined as y compound that comprises at least two primary amine functions.

As an acrylate, it is possible to use, for example, triacrylates (such as C$_{15}$O$_6$H$_{20}$, CAS no. 15625-89-5); tetraacrylates; pentaacrylates; hexaacrylates; mixtures between these different acrylates mentioned. Molecules of the type O[CH$_2$C(CH$_2$OR)$_3$]$_2$, where R can be H, or COCH=CH$_2$, can, for example, be used.

As an amine, it is possible to use, by way of example, molecules of the type NH$_2$(CH$_2$)$_n$NH$_2$ where n is an integer that can typically be comprised between 1 and 20, and which can be, for example, 2 (ethylene diamine) or 6 (hexamethylene diamine, CAS number: 124-09-4). Piperazine, meta-xylylene diamine, pentaethylenehexamine, tris(2-aminoethyl)amine (TREN), or polyethyleneimine (PEI) can also be used.

The nature and the concentration of the amines and acrylates can be varied.

The ratio of the reactive functions of the monomers Y (—NH) and X (acrylate) is, advantageously, greater than 1, and, typically, comprised between 1 and 5, preferably, between 1.2 and 3.8.

According to a particular embodiment of the invention, the monomers X (acrylate) and/or Y (amine) are bio-sourced.

Figure 6:
FIG. 6 shows the reaction scheme of the reaction according to the invention.
Figure 6:
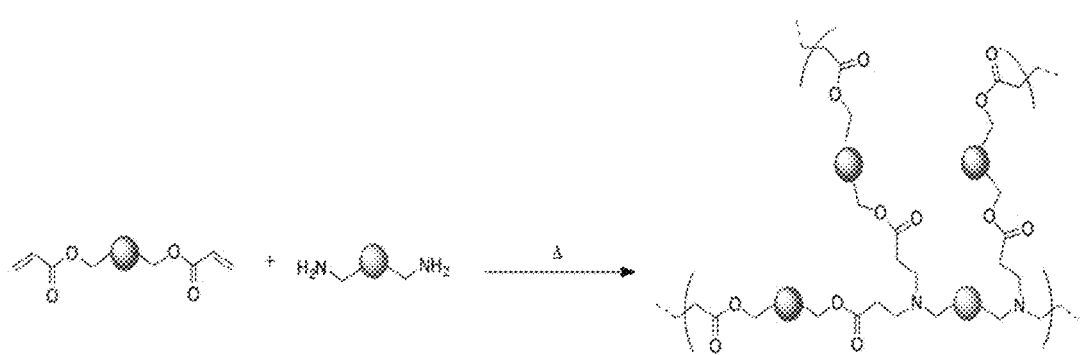

FIG. 6 shows the reaction scheme of the aza-Michael addition reaction between a secondary amine and an acrylate (reaction (a)) and of the polyaddition reaction between a multifunctional acrylate compound, and a multi-amine compound, leading to a crosslinked polymer (reaction (b)).

The organic core of the microcapsules can be formed from an organic phase comprising an active substance. During the formation of the microcapsule, this organic (oily) phase will be enclosed by the polymeric wall of the microcapsule, which protects it from the environment. Said organic (oily) phase can consist of said active substance, or said active substance can be part of said organic (oily) phase, wherein it can, in particular, be dissolved. The expression "active substance" refers here to the precise purpose, wherein the microcapsules are intended to be used; as a general rule, in light of the specificity of the microcapsule product, this purpose is always known during the manufacturing thereof.

The active substance can be selected, in particular, from oils (pure or possibly containing other molecules in solution or in dispersion), such as essential oils, natural and edible oils, vegetable and edible oils, liquid alkanes, esters and fatty acids, or from dyes, inks, paints, thermochromic and/or photochromic substances, fragrances, biocidal effect products, fungicide effect products, antiviral effect products, phytosanitary effect products, pharmaceutical active ingredients, cosmetic effect products, glues; these active principles optionally being in the presence of an organic vector.

It is possible to use, for example, and in a non-limiting way, natural product distillation products such as the essential oils of *eucalyptus*, lemongrass, lavender, mint, cinnamon, camphor, aniseed, lemon, orange, which have been obtained by extraction from plant material, or by synthesis.

Other substances can also be used, such as long-chain alkanes (for example, tetradecane), which can contain lipophilic molecules in solution.

Generally, and according to the function sought for the microcapsules, it is possible to use any hydrophobic compound, which will, thus, be dispersed naturally in the form of an emulsion of hydrophobic drops, in suspension, in an aqueous phase.

Many additives can be incorporated into the microcapsule, which allow for better protection of the organic (oily) phase to be encapsulated, from infrared radiation, ultraviolet radiation, and involuntary penetration of a specific gas or oxidation.

The shell of the microcapsules can be modified by applying a surface coating. The deposition of said coating can be carried out by adding a polymer dispersed in an aqueous phase which will the boat the surface. Among the polymers that can be used to this end, polysaccharides (cellulose, starch, alginates, chitosan) and their derivatives can be mentioned. This addition can be made at elevated temperature, or at room temperature, at the end of the interfacial polymerization.

The shell of the microcapsules can also be modified by adding a radical initiator, either to the aqueous phase, or in the organic (oily) phase. Their addition to the organic phase can be carried out before, and/or after, the preparation of the PBAE shell. When the radical initiators are added after the preparation of the shell, the radial initiator can be diluted in acetone, in order to favor its penetration into the microcapsules. Said initiators can be azoic compounds (such as azobis-isobutyronitrile, and its derivatives), or peroxidic compounds (such as lauroyl peroxide). When the radical initiators are added to the aqueous phase, the initiators can, in particular, be water soluble azoic compounds (such as 2,2'-Azobis(2-methylpropionamidine) dihydrochloride), or redox systems (such as ammonium or potassium persulfate, in combination with potassium metabisulfite). Under an inert atmosphere, the radicals generated by the decomposition of the radical initiators can react with the residual acrylate functions in the PBAE shell, and thereby increase its mechanical strength and/or modify its polarity.

Another way to modify the shell of the microcapsules is to make their residual amine functions on the surface react with water soluble monofunctional acrylates. While the inventors do not wish to be bound by this theory, they believe that, through a Michael addition, amino-ester bondings are formed, which can fix a functional group onto the surface. Among the water soluble acrylates that can be used, the following examples can be mentioned: acrylic acid, 2-carboxyethyle acrylate, 2-(dimethylamino)ethyl acrylate, 2-hydroxyethyle acrylate, poly(ethylene glycol) acrylates, and the potassium salt of 3-sulfopropyl acrylate.

As a surfactant agent, use can be made, in particular, of those which are mentioned in the *Encyclopedia of Chemical Technology*, volume 8, pages 912 to 915, and which have a lipophilic hydrophilic balance (according to the HLB system) greater than or equal to 10.

Other macromolecular surfactants can also be used. Mention can be made, for example, of polyacrylates, methylcelluloses, carboxymethylcelluloses, polyvinyl alcohol (PVA), optionally partially esterified or etherified, polyacrylamide, or synthetic polymers that have anhydride or carboxylic acid functions, such as ethylene/maleic anhydride copolymers. Preferably, polyvinyl alcohol can be used as a surfactant agent.

It can be necessary, for example in the case of aqueous solutions of a cellulosic compound, to add a small amount of alkaline hydroxide, such as soda, in order to facilitate the dissolution thereof; it is also possible to directly use such cellulosic compounds in the form of the sodium salts thereof, for example. Amphiphilic copolymers of the Pluronics® type can also be used. Generally, aqueous solutions containing from 0.1 to 5% by weight of surfactant are used.

The size of the droplets is according to the nature and the concentration of the surfactant, and the stirring speed, with the latter being chosen all the more so large as the desire to obtain smaller average diameters of droplets.

In general, the stirring speed during the preparation of the emulsion is from 5,000 to 10,000 revolutions per minute. The emulsion is usually prepared at a temperature comprised between 15° C. and 95° C.

Generally, when the emulsion has been obtained, stirring by turbine is stopped, and the emulsion is stirred using a slower stirrer of the current type, for example, of the frame stirrer type, typically at a speed of about 150 to 1,500 revolutions per minute. The method according to the invention thus leads to homogeneous and fluid suspensions containing, according to the charges introduced, generally from 20% to 80% by weight of microcapsules having from 100 nm to 100 µm in average diameter. The diameter of the microcapsules can, preferably, be comprised between 1 µm and 50 µm, and even more preferably between 10 µm and 40 µm.

It is also possible to vary the proportion of the encapsulated organic phase.

The microcapsules according to the invention, and, in particular, their wall, are (bio)degradable. The biodegradation can be determined, for example, by one of the methods described in document "*OECD Guidelines for Testing of Chemicals: Ready Biodegradability*" (adopted by the OECD Council on Jul. 17, 1992). It is possible to use, in particular, the manometric respirometry test (method 301 F). Preferably, this test is implemented on washed and emptied microcapsules, so that the biodegradation of the contents of the microcapsules does not interfere with the test of which the purpose is to characterize the biodegradation of the material forming the wall of the microcapsules.

Preferably, the microcapsule according to the invention and/or its wall shows a biodegradation of at least 80%, preferably of at least 83%, and more preferably of at least 85%, measured after an incubation of 10 days using said method 301 F. With this same method, after an incubation of 28 days, the microcapsules, according to the invention, preferably show a biodegradation of at least 90%, preferably of at least 95%, and even more preferably of at least 98%.

EXAMPLES

In order to allow those skilled in the art to reproduce the invention examples of embodiments are given here; they do not limit the scope of the invention.

Example 1: Preparation of Scented Microcapsules with a Diamine Base (HMDA)

(i) Preparation of the Emulsion 11.0 g of essential oil (*Eucalyptus*) were placed in a beaker, and the multi-acrylate monomer (dipentaerythritol penta-/hexa-acrylate mixture) (0.39 g, 0.71 mmol) was dispersed in essential oil under magnetic stirring (350 rpm). The stirring was maintained until the solution became homogeneous; a step of heating was added if necessary. The essential oil/organic monomer assembly was progressively added to the aqueous solution of the surfactant prepared beforehand (40 g, PVA 2% by weight); the mixture was homogenized using an IKA T10 ULTRA-TURRAX® homogenizer at 9,500 rpm for 3 min at ambient temperature in order to form an emulsion.

(ii) Microencapsulation

In a double-wall reactor, equipped with an IKA mechanical blade stirring system, preheated to 50° C., the previously prepared emulsion was introduced and stirred at a speed of 250 rpm. When the emulsion reached 50° C., the diamine solution (hexamethylene diamine HMDA) (0.17 g, 1.46 mmol) in 5 g of 2 wt % PVA solution was added drop by drop using a syringe and under stirring (250 rpm). During the reaction, samples at different times of the reaction were taken and analyzed by optical microscopy and Fourier transform infrared spectroscopy (FTIR) in order to follow the formation of the microcapsules.

The total quantity of monomers used was ~0.56 g. The amine was used in excess with respect to the acrylate monomer in such a way as to have a —NH/acrylate function ratio=1.6. The essential oil/water mass ratio is equal to 0.24.

The analysis of the microcapsules can be done by microscopy after a step of drying. This analysis makes it possible to ensure the stability of the microcapsules once isolated. A second analysis consists of adding a few drops of a fluorescent dye (Nile Red) on the dried microcapsules. Nile Red, a lipophilic chromophore that is fluorescent only in an organic phase, makes it possible to verify that the core of the microcapsule still contains an organic phase and that the microcapsules are filled.

Figure 2:
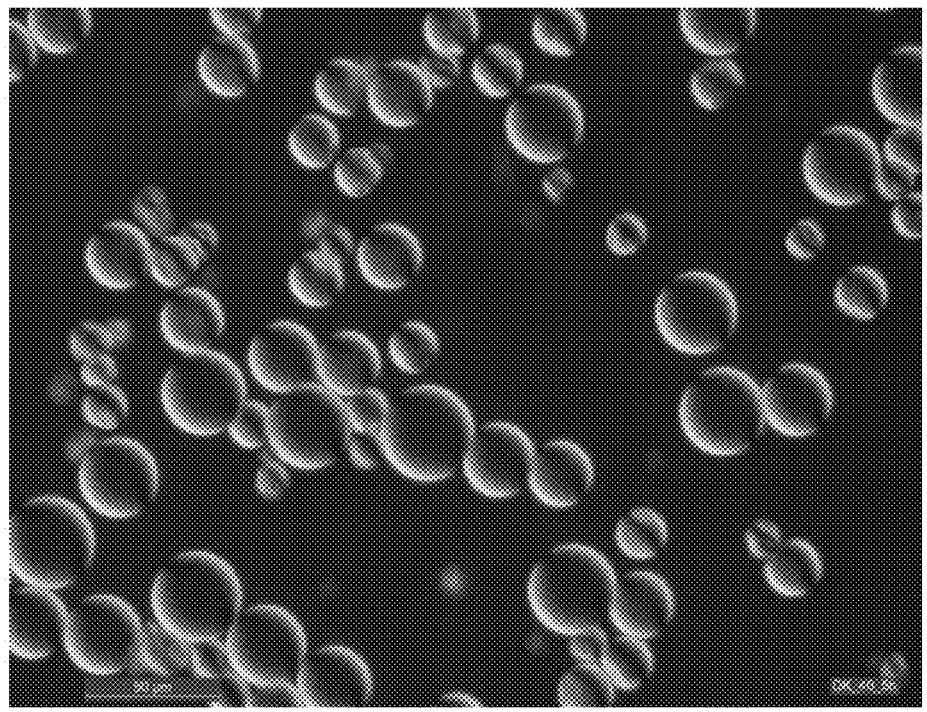
FIG. 2 shows an optical micrograph of microcapsules obtained according to Example 1, after 5 hours of reaction.
Figure 3:
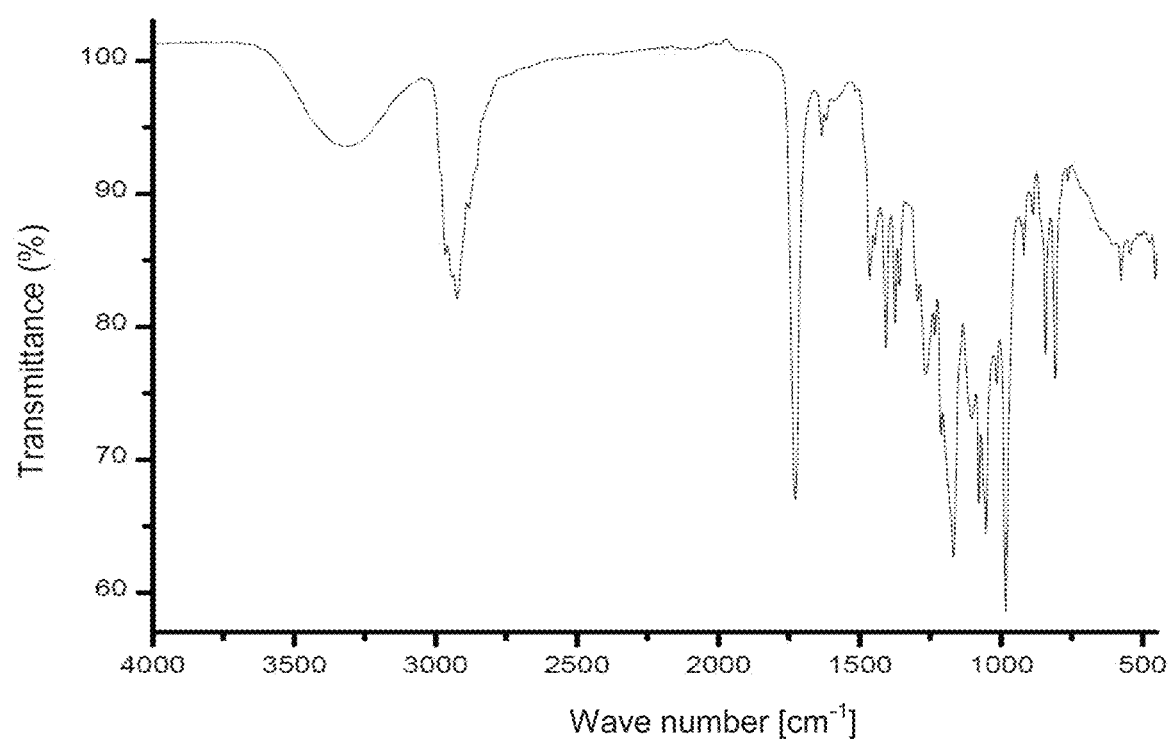
FIG. 3 shows an FTIR spectrum of the wall of microcapsules isolated in the slurries after 6 hours of reaction.

FIG. 2 shows an optical microscopy image of the reaction medium after 5 h of reaction. The microcapsules are spherical, with a diameter comprised between about 10 µm and about 25 µm. FIG. 3 shows the FTIR spectrum of the isolated microcapsules of a slurry after 6 h of reaction (after washing with acetone, followed by three cycles of centrifugation and oven drying). Vibrations characteristic of N—H bonds around 3,300 $cm^{-1}$ to 3,400 $cm^{-1}$ are noted, as well as a narrow band characteristics of a C═O bond around 1,727 $cm^{-1}$.

Figure 4:
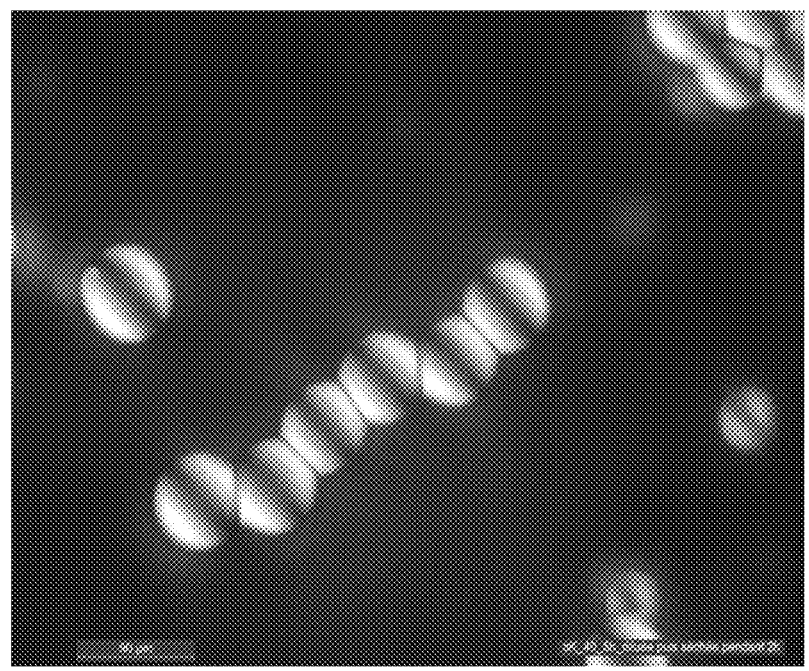
FIG. 4 shows an optical micrograph of microcapsules obtained according to Example 1, after drying on a glass slide.
Figure 5:
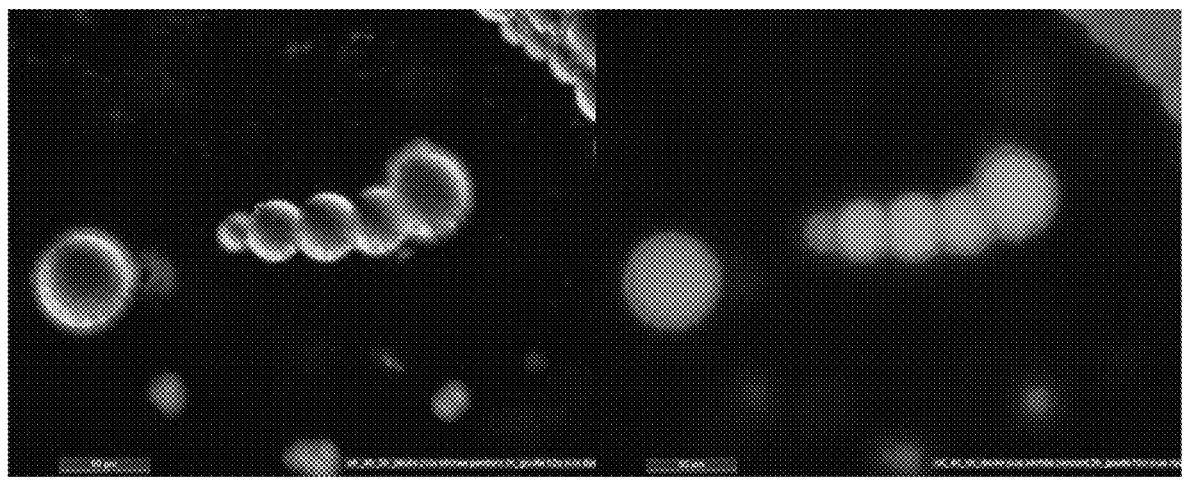
FIG. 5 shows two optical micrographs of microcapsules obtained according to Example 1, after drying on a glass slide. The micrograph on the left was obtained under low-angled light, the micrograph on the right under fluorescent light after adding a few drops of a fluorescent dye.

FIG. 4 shows an optical micrograph of microcapsules dried on a glass slide. The diameter thereof is about 30 µm to 35 µm. FIG. 5 shows a micrograph of microcapsules dried on a glass slide under low-angled light (on the left) and under fluorescent light (on the right) after adding a few drops of the fluorescent dye Nile Red. The intense emission under fluorescent light shows that the core of the microcapsule contains an organic phase.

Example 2: Preparation of Scented Microcapsules with a Diamine Base (NMDA)

(i) Preparation of the Emulsion 11.0 g of a thermo-chromic solution (blue 10°) were introduced into a beaker, placed in an oil bath and heated to 130° C. under magnetic stirring (350 rpm). The stirring was maintained until the thermo-chromic solution became homogeneous and transparent. The thermo-chromic solution was cooled, and when the temperature thereof reached 50° C., the (multi)acrylate monomer (dipentaerythritol penta-/hexa-acrylate mixture) (0.39 g, 0.71 mmol) is dispersed under magnetic stirring (350 rpm). The stirring is maintained until the solution becomes homogeneous. The thermo-chromic/organic monomer assembly was progressively added to the aqueous solution of the surfactant prepared beforehand (40 g, PVA 2% by weight); the mixture was homogenized using an IKA T10 ULTRA-TURRAX® homogenizer at 9,500 rpm for 3 min, at ambient temperature in order to form an emulsion (ii) Microencapsulation In a double-wall reactor, equipped with an IKA mechanical blade stirring system, preheated to 50° C., the previously prepared emulsion was introduced and stirred at a speed of 250 rpm. When the emulsion reached 50° C., the diamine solution (hexamethylene diamine HMDA) (0.17 g, 1.46 mmol) in 5 g of 2 wt % PVA solution was added drop by drop using a syringe and under stirring (250 rpm). During the reaction, samples at different times of the reaction were taken and analyzed by optical microscopy.

The total quantity of monomers used was ~0.56 g. The amine was used in excess with respect to the acrylate monomer in such a way as to have a —NH/acrylate function ratio=1.6. The mass ratio of the thermo-chromic/water solution is 0.24.

The dried microcapsules reveal a reversible change in color with a reversible change in color at a temperature to 10° C. These same capsules can, in addition, be heated in the oven at 130° C. for 30 min without modifications in the thermochromism properties thereof (FIG. 7).

Example 3: Degradability Test of a Poly(Beta-Amino Ester)

A first degradability test was carried out according to the following procedure:
(1) Synthesis of Poly(Beta-Amino Ester)

In a beaker, the hexamethylene diamine monomer HMDA (1.0 g, 8.6 mmol) was solubilized in THF (4.0 g) and added to a solution of the (multi)acrylate monomer (trimethylolpropane triacrylate) (1.8 g, 6.1 mmol) solubilized in 2.5 g of THF. The mixture was placed in a pill box then placed in an oil bath at 50° C.

The amine was used in excess with respect to the acrylate monomer in such a way as to have a —NH/acrylate function ratio=2.

The polymer recovered after 5 h of reaction was washed three times with acetone and oven dried.
(2) Degradation of the Poly(Beta-Amino Ester)

The degradation of the poly(beta-aminoester) was carried out according to the following protocol:

20 mg of polymer solubilized in 1 mL of a sodium hydroxide solution (3M, in semiheavy water $D_2O$, pH~14) is introduced into a bottle provided with a magnetic stirrer. As the polymer is crosslinked, it is not soluble in the aqueous phase.

Figure 8:
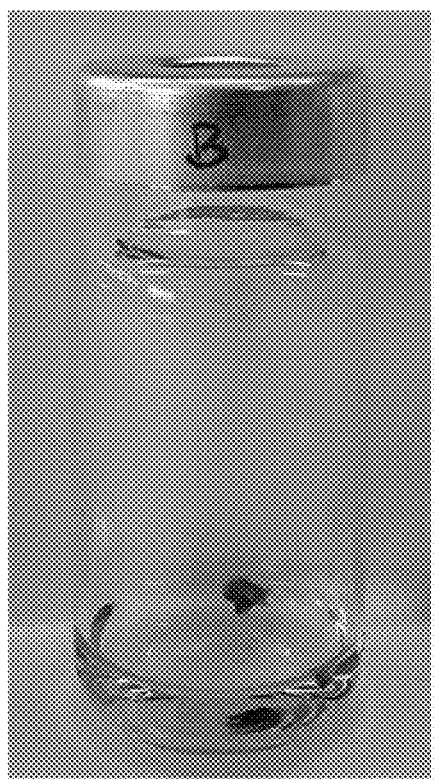
FIG. 8 shows the degradability of the walls of the microcapsule by an accelerated degradation test.
Figure 8:
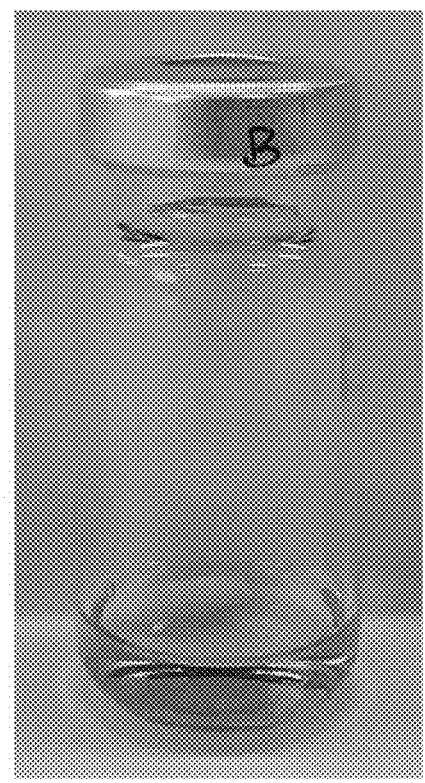

FIG. 8 shows that the poly(beta-amino ester) dissolved in the aqueous phase, characterizing an effective degradation of the polymer in these conditions of accelerated degradation.

Example 4: Preparation of Scented Microcapsules with a Triamine Base (TREN)

(i) Preparation of the Emulsion 11.0 g of essential oil (*Eucalyptus*) were placed in a beaker, and the multi-acrylate monomer (dipentaerythritol penta-/hexa-acrylate mixture) (0.39 g, 0.74 mmol) was dispersed in the essential oil under stirring. The essential oil/organic monomer assembly was progressively added to the aqueous solution of the surfactant prepared beforehand (40 g, PVA 2% by weight); the mixture was homogenized using an IKA T10 ULTRA-TURRAX® homogenizer in order to form an emulsion.

(ii) Microencapsulation

In a double-wall reactor, equipped with an IKA mechanical blade stirring system, the emulsion prepared beforehand was introduced therein. An aqueous solution of tris(2-aminoethyl)amine TREN (0.145 g, 0.99 mmol) in 5 g of 2 wt % PVA solution was added under stirring at a temperature comprised between 50° C. and 60° C.

Example 5: Preparation of Thermochromic Microcapsules with a Triamine Base (TREN)

(i) Preparation of the Emulsion 11.0 g of a thermochromic solution were introduced into a beaker and hot stirred, the multi-acrylate monomer (dipentaerythritol penta-/hexa-acrylate mixture) (0.39 g, 0.74 mmol) was dispersed therein under stirring. The thermochromic/organic monomer assembly was progressively added to the aqueous solution of the surfactant prepared beforehand (40 g, PVA 2% by weight); the mixture was homogenized using an IKA T10 ULTRA-TURRAX® homogenizer in order to form an emulsion.

(ii) Microencapsulation

In a double-wall reactor, equipped with an IKA mechanical blade stirring system, the previously prepared emulsion was introduced at a temperature of about 50° C. to 60° C. An aqueous solution of tris(2-aminoethyl) amine TREN (0.145 g, 0.99 mmol) in 5 g of 2 wt % PVA solution was added under stirring at a temperature comprised between 50° C. and 80° C.

Example 6: Preparation of Microcapsules with a Biogenic Monomer Base (i) Preparation of the Emulsion 11.0 g of essential oil (*Eucalyptus*) were placed in a beaker, and the multi-acrylate monomer (dipentaerythritol penta-/hexa-acrylate mixture) (0.39 g, 0.74 mmol) was dispersed in the essential oil under stirring. The essential oil/organic monomer assembly was progressively added to the aqueous solution of the surfactant prepared beforehand (40 g PVA 2% by weight); the mixture was homogenized using an IKA T10 ULTRA-TURRAX® homogenizer in order to form an emulsion.

(ii) Microencapsulation

Figure 10:
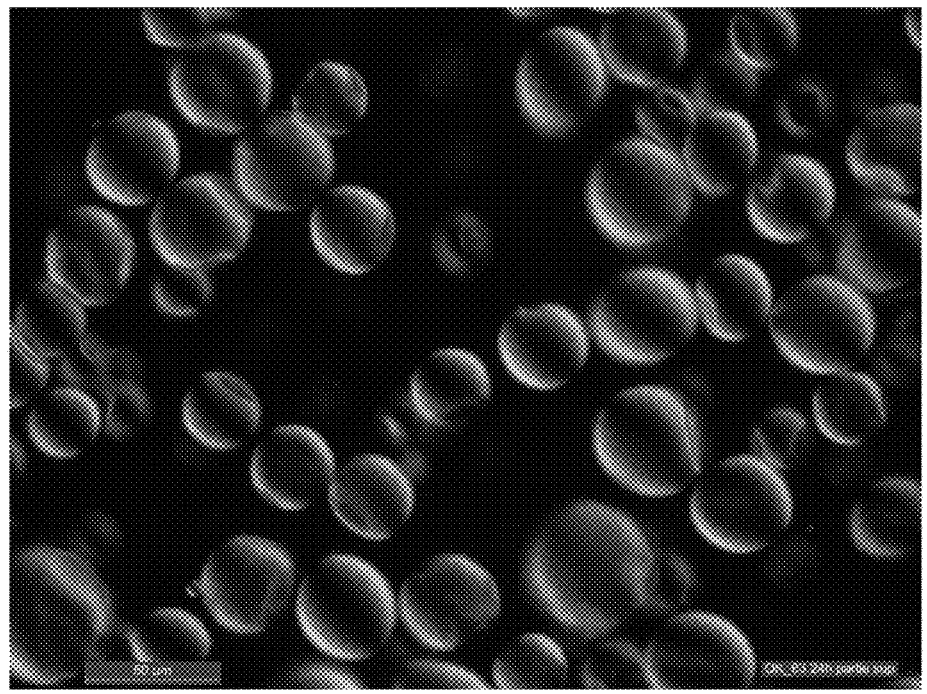
FIG. 10 shows that the microcapsules are stable after 24 h, and the average diameter thereof is comprised between 10 µm and 30 µm.

In a double-wall reactor, equipped with an IKA mechanical blade stirring system, the previously prepared emulsion was introduced, the aqueous solution of diamine (Butane-1,4-diamine (Putrescine) (0.13 g, 1.47 mmol) in 5 g of 2 wt % PVA solution was added under stirring at a temperature comprised between 50° C. and 60° C. FIG. 10 shows an optical microscopy image of capsules after 24 h of reaction. The microcapsules are spherical, with an average diameter comprised between about 10 µm and about 30 µm.

Example 7: Preparation of Microcapsules with a Polyethyleneimine Base (PEI)

(i) Preparation of the Emulsion 11.0 g of essential oil (*Eucalyptus*) were placed in a beaker, and the multi-acrylate monomer (dipentaerythritol penta-/hexa-acrylate mixture) (0.39 g, 0.74 mmol) was dispersed in the essential oil under stirring. The essential oil/organic monomer assembly was progressively added to the aqueous solution of the surfactant prepared beforehand (40 g PVA 2% by weight); the mixture was homogenized using an ULTRA-TURRAX® homogenizer IKA in order to form an emulsion.

(ii) Microencapsulation

In a double-wall reactor, equipped with an IKA mechanical blade stirring system, the previously prepared emulsion was introduced. A polyethyleneimine solution (PEI) (1.78 g, 1.48 mmol) in 5 g of 2 wt % PVA solution was added under stirring at a temperature comprised between 50° C. and 60° C.

Figure 11:
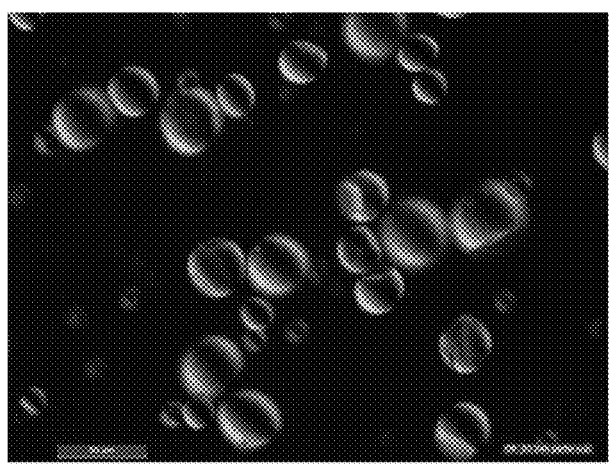
FIG. 11 shows an image similar to FIG. 10, and leads to the same conclusion, for another example.
Figure 11:
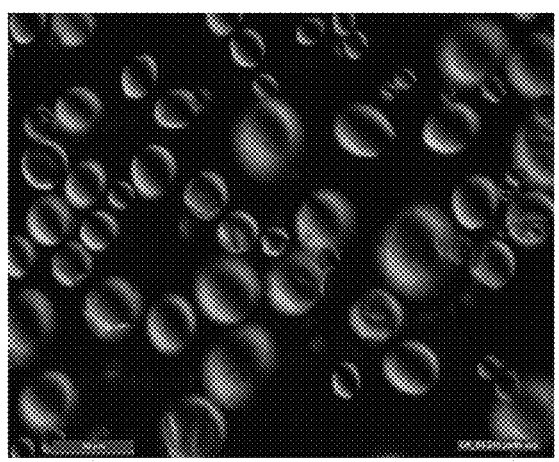

FIG. 11 shows optical microscopy images of capsules after 24 h of reaction. The microcapsules are spherical, with an average diameter comprised between about 10 µm and about 30 µm

Example 8: Preparation of Scented Microcapsules (Shell/PI Ratio=3.4%)

(i) Preparation of the Emulsion 193.6 g of essential oil (*Eucalyptus*) were placed in a beaker, and the multi-acrylate monomer (dipentaerythritol penta-/hexa-acrylate mixture) (4.5 g, 8.5 mmol) was dispersed in the essential oil under stirring. The essential oil/organic monomer assembly was progressively added to the aqueous solution of the surfactant prepared beforehand (255.9 g PVA 2% by weight); the mixture was homogenized in order to form an emulsion.

(ii) Microencapsulation

In a double-wall reactor, equipped with an IKA mechanical blade stirring system, the previously prepared emulsion was introduced. A diamine solution (hexamethylene diamine HMDA) (2.01 g, 17.2 mmol) in 44.1 g of a 2 wt % PVA solution was added under stirring at a temperature comprised between 50° C. and 60° C. It was allowed to react for 2 h at 50° C. and for 5 h at 60° C.

Example 9: Preparation of Scented Microcapsules (i) Preparation of the Emulsion 11.0 g of a mixture of 80% Pineapple *papaya* scent (reference RS42370 from the company Technicoflor at Allauch (France)) and 20% methyl myristate were placed in a beaker, and the multi-acrylate monomer (dipentaerythritol penta-/hexa-acrylate mixture) (0.39 g, 0.74 mmol) was dispersed in the fragrance under stirring. The fragrance/organic monomer assembly was progressively added to the aqueous solution of the surfactant prepared beforehand (40 g PVA 2% by weight); the mixture was homogenized using an IKA T10 ULTRA-TURRAX® homogenizer in order to form an emulsion.

(ii) Microencapsulation

In a double-wall reactor, equipped with an IKA mechanical blade stirring system, the previously prepared emulsion was introduced. A diamine solution (hexamethylene diamine HMDA) (0.17 g, 1.49 mmol) in 5 g of a 2 wt % PVA solution was added under stirring at a temperature comprised between 50° C. and 60° C. It was allowed to react for 2 h at 50° C. and for 5 h at 60° C.

Example 10: Preparation of Microcapsules for Carbonless Paper (Ratio Shell/PI=3.4%)

(i) Preparation of the Emulsion 193.6 g of an internal phase (dye) were placed in a beaker, and the multi-acrylate monomer (dipentaerythritol penta-/hexa-acrylate mixture)(4.5 g, 8.5 mmol) was dispersed in the internal phase under stirring. The assembly was progressively added to the aqueous solution of the surfactant prepared beforehand (255.9 g, PVA 2% by weight); the mixture was homogenized in order to form an emulsion.

(ii) Microencapsulation

In a double-wall reactor, equipped with an IKA mechanical blade stirring system, the previously prepared emulsion was introduced. An aqueous solution of diamine (hexamethylene diamine HMDA) was added, under stirring at a temperature comprised between 50° C. and 60° C.

(iii) Use of Microcapsules in a Carbonless Paper

Figures 9, 12:
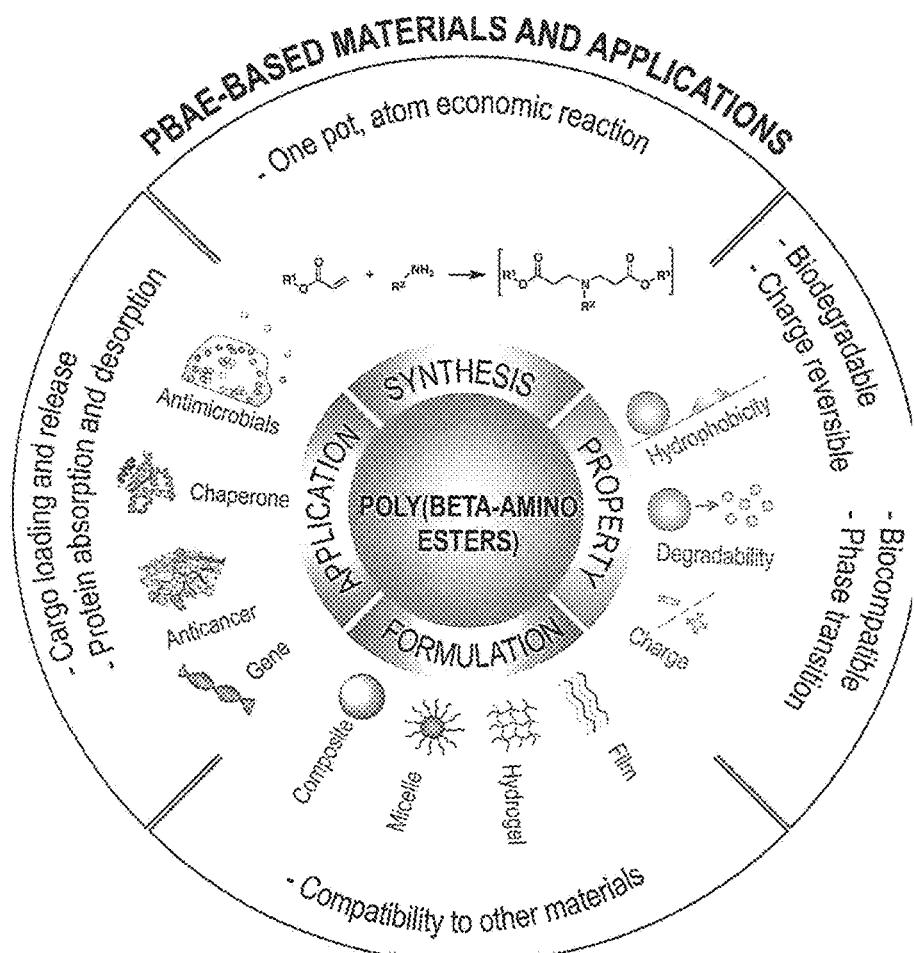
FIG. 9 shows the various fields of application of poly (beta-amino ester)s.
FIG. 12 shows the result of the use of microcapsules according to the invention in a carbonless paper.

These microcapsules were applied on a sheet of paper, according to known methods, and were used in a copying system. FIG. 12 shows the result, which is entirely satisfactory.

Example 11: Preparation of Thermochromic Microcapsules with a POSS@Octa(Acrylate) Monomer Base (i) Preparation of the Emulsion 20.0 g of thermochromic, and the polyoctahedral silsesquioxanes carrying eight acrylate function (POSS@octa (acrylate), CAS no. 1620202-27-8, purchased from Hydridplastics, 1.48 g, 1.12 mmol) and the thermal inhibitor Butylated HydroxyToluene (BHT, 5.0 mg), were placed in a beaker. The mixture was hot solubilized under magnetic stirring. The stirring was maintained until the solution became homogeneous. The thermochromic/POSS@octa (acrylate) assembly was progressively added to the aqueous solution of the surfactant prepared beforehand (40 g, PVA 2% by weight); the mixture was homogenized using an IKA T10 ULTRA-TURRAX® homogenizer in order to form an emulsion.

(ii) Microencapsulation

In a reactor, the previously prepared emulsion was introduced. The hexamethylene diamine solution (NMDA, 0.35 g, 3.01 mmol) in water was added drop by drop using a syringe and under stirring. It was allowed to react at 50° C. for 1 h and at 80° C. for 23 h.

Figure 13:
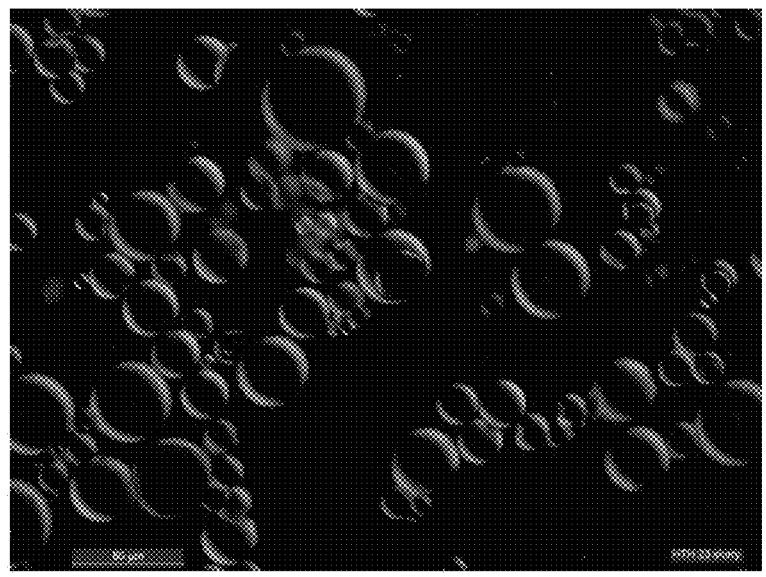
FIG. 13 shows a photograph of microcapsules according to yet another example of the invention.

FIG. 13 shows a photograph of these microcapsules.

Example 12: Preparation of Thermochromic Microcapsules with a POSS@Octa(Acrylate) Monomer Base with Meta-Xylylenediamine (i) Preparation of the Emulsion 10.0 g of thermochromic, and the polyoctahedral silsesquioxanes carrying eight acrylate function (POSS@octa (acrylate), CAS no. 1620202-27-8, purchased from Hydridplastics, 1.50 g, 1.12 mmol) and the thermal inhibitor Butylated HydroxyToluene (BHT, 5.0 mg), were placed in a beaker. The mixture was hot solubilized under magnetic stirring. The stirring was maintained until the solution became homogeneous. The thermochromic/POSS@octa (acrylate) assembly was progressively added to the aqueous solution of the surfactant prepared beforehand (40 g, PVA 2% by weight); the mixture was homogenized using an IKA T10 ULTRA-TURRAX® homogenizer in order to form an emulsion.

(ii) Microencapsulation

In a reactor, the previously prepared emulsion was introduced. The meta-xylylenediamine solution (CAS no. 1477-55-0, 0.60 g, 3.01 mmol) in 3 mL of water was added drop by drop using a syringe and under stirring. It was allowed to react at 65° C. for 1 hand at 80° C. for 17 h.

Example 13: Preparation of Thermochromic Microcapsules with a POSS@Octa(Acrylate) Monomer Base with POSS@Octammonium and Hexamethylene Diamine (HDMA)

(i) Preparation of the Emulsion 10.0 g of thermochromic, and the polyoctahedral silsesquioxanes carrying eight acrylate function (POSS@octa (acrylate), CAS no. 1620202-27-8, purchased from Hydridplastics, 1.40 g, 1.06 mmol) and the thermal inhibitor Butylated HydroxyToluene (BHT, 5.0 mg), were placed in a beaker. The mixture was hot solubilized under magnetic stirring. The stirring was maintained until the solution became homogeneous. The thermochromic/POSS@octa (acrylate) assembly was progressively added to the aqueous solution of the surfactant prepared beforehand (40 g, PVA 2% by weight); the mixture was homogenized using an IKA T10 ULTRA-TURRAX® homogenizer in order to form an emulsion.

(ii) Microencapsulation

In a reactor, the previously prepared emulsion was introduced. After, the Hexamethylene diamine solution (NMDA, 0.70 g, 6.02 mmol), POSS@(octa)ammonium (CAS no. 150380-11-3, purchased from Hydridplastics, 0.30 g, 0.26 mmol), and potassium carbonate (0.16 g, 1.16 mmol) in water was added drop by drop using a syringe, under stirring. It was allowed to react at 65° C. for 1 h and at 80° C. for 17 h.

Figure 14:
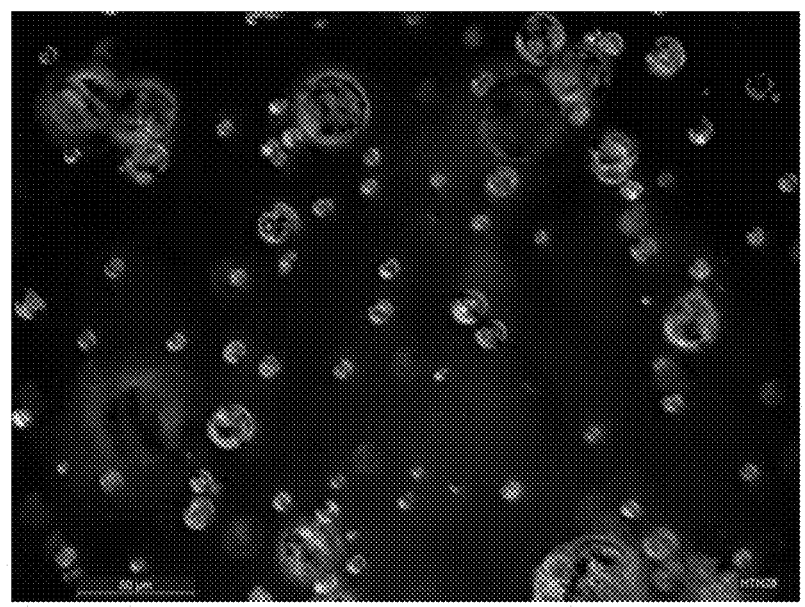
FIG. 14 shows a photograph of microcapsules according to yet another example of the invention.
Figure 15:
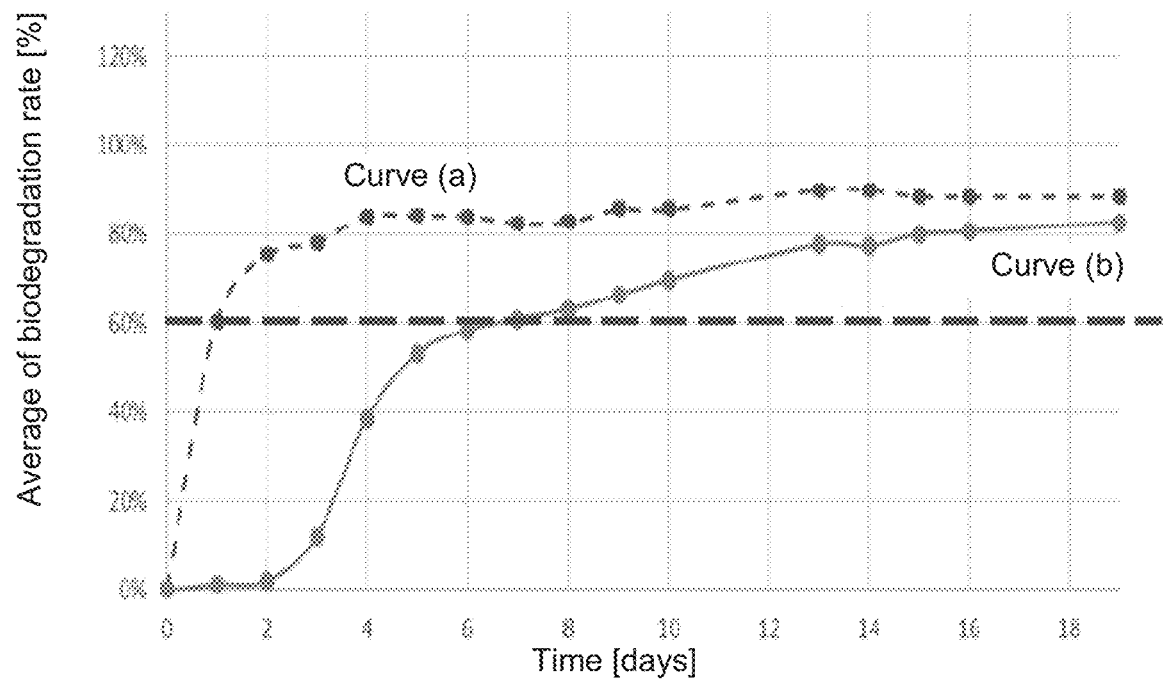
FIG. 15 shows the percentage of biodegradation as a function of time for dry microcapsules according to the invention.

FIG. 14 shows a photograph of these microcapsules.

Example 14: Biodegradation Test

A batch of microcapsules prepared according to Example 8 was supplied. The dry microcapsules contained an essential oil (*Eucalyptus*). They were subjected to the biodegradability test as described in document OECD 301 ("*OECD Guidelines for Testing of Chemicals: Ready Biodegradability*") by using the method 301 F (Manometric respirometry test). After an incubation duration of nineteen days the percentage of biodegradation was 83%.

FIG. 15 shows the evolution of the percentage of biodegradation as a function of time, over 19 days. Curve (b) corresponds the microcapsules, while curve (a) corresponds to a reference product (sodium acetate) that was treated separately under the same conditions of biodegradation.

Example 15: Biodegradation Test

Figure 16:
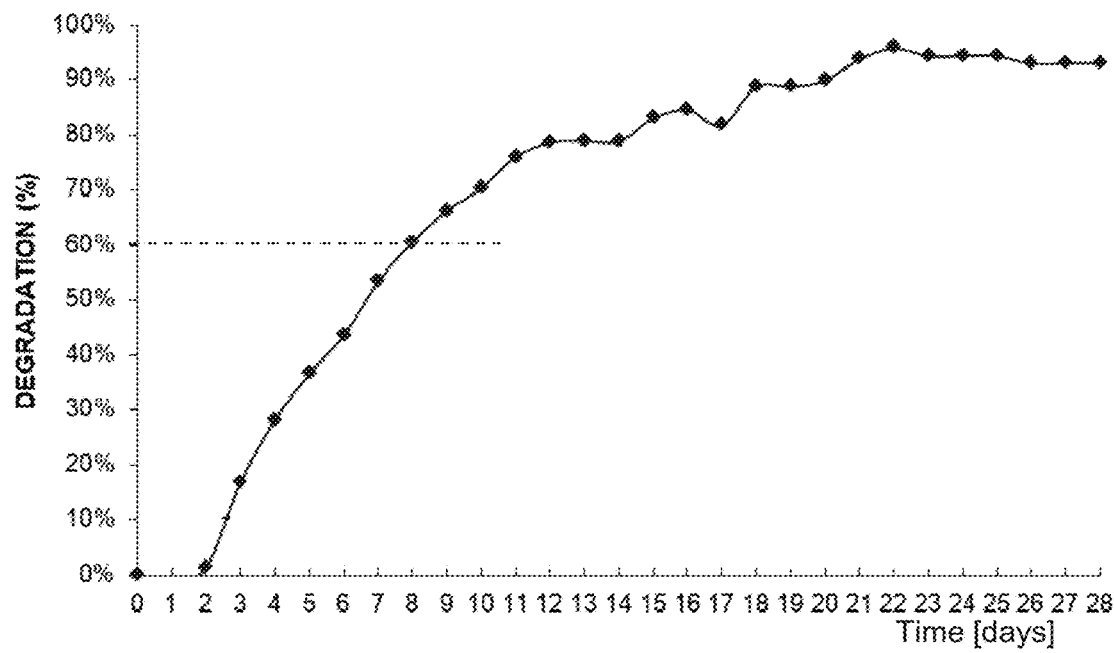
FIG. 16 shows the percentage of biodegradation as a function of time for the shell of microcapsules according to the invention.

A batch of microcapsules prepared according to example 8 was supplied. The microcapsules were opened, emptied and washed. Then they were subjected to the biodegradability test as described in document OECD 301 ("*OECD Guidelines for Testing of Chemicals: Ready Biodegradability*") by using the method 301 F (Manometric respirometry test). After an incubation duration of ten days the percentage of biodegradation was 93%. FIG. 16 shows the evolution of the percentage of biodegradation as a function of time.

Example 16: Preparation of Scented Microcapsules Based on a Multiamine (Pentaethylenehexamine)

(i) Preparation of the Emulsion 19.7 g of essential oil (*Eucalyptus*) were placed in a beaker, and the multi-acrylate monomer (dipentaerythritol penta-/hexa-acrylate mixture) (1.2 g, 2.29 mmol) was dispersed in the essential oil under magnetic stirring (350 rpm) at 50° C. Stirring was maintained until the solution became homogeneous. The essential oil/organic monomer assembly was progressively added to the aqueous solution of the surfactant prepared beforehand (31.7 g, PVA 2% by weight) and preheated at 50° C.; the mixture was homogenized using an ULTRA-TURRAX® homogenizer IKA T10 at 11,500 rpm for 3 min at 50° C. in order to form an emulsion.

(ii) Microencapsulation

In a double-wall reactor, equipped with an IKA mechanical blade stirring system, preheated at 50° C., the previously prepared emulsion was introduced and stirred at a speed of 250 rpm. A multiamine solution (pentaethylenehexamine) (1.9 g, 8.00 mmol) in 5.5 g of a 2 wt % PVA solution was added drop by drop using a syringe under stirring at 250 rpm. The mixture was maintained stirred for two hours at 50° C. and the for 5 hours at 60° C. The total quantity of monomer used was 3.1 g. The amine was used in excess with respect to the acrylate monomer such as to have a molar ratio amine/acrylate of 3.5. The weight ratio essential oil/water was 0.53.

Example 16: Preparation of Scented Microcapsules Based on a Multiamine (Pentaethylenehexamine)

(i) Preparation of the Emulsion 19.7 g of essential oil (*Eucalyptus*) were placed in a beaker, and the multi-acrylate monomer (dipentaerythritol penta-/hexa-acrylate mixture) (1.2 g, 2.29 mmol) was dispersed in the essential oil under magnetic stirring (350 rpm) at 50° C. Stirring was maintained until the solution became homogeneous. The essential oil/organic monomer assembly was progressively added to the aqueous solution of the surfactant prepared beforehand (31.7 g, PVA 2% by weight) and preheated at 50° C.; the mixture was homogenized using an ULTRA-TURRAX® homogenizer IKA T10 at 11,500 rpm for 3 min at 50° C. in order to form an emulsion.

(ii) Microencapsulation

In a double-wall reactor, equipped with an IKA mechanical blade stirring system, preheated at 50° C., the previously prepared emulsion was introduced and stirred at a speed of 250 rpm. A multiamine solution (pentaethylenehexamine) (1.9 g, 8.00 mmol) in 5.5 g of a 2 wt % PVA solution was added drop by drop using a syringe under stirring at 250 rpm. The mixture was maintained stirred for two hours at 50° C. and the for 5 hours at 60° C. The total quantity of monomer used was 3.1 g. The amine was used in excess with respect to the acrylate monomer such as to have a molar ratio amine/acrylate of 3.5. The weight ratio essential oil/water was 0.53.

Example 17: Preparation of Scented Microcapsules Based on an Aromatic Diamine (m-Xylene Amine)

(i) Preparation of the Emulsion 22.0 g of fragrance were placed in a beaker, and the multi-acrylate monomer (dipentaerythritol penta-/hexa-acrylate mixture) (1.52 g, 2.90 mmol) was dispersed in the fragrance under magnetic stirring (350 rpm) at 50° C. Stirring was maintained until the solution became homogeneous. The fragrance/organic monomer assembly was progressively added to the aqueous solution of the surfactant prepared beforehand (35.0 g, PVA 2% by weight); the mixture was homogenized using an ULTRA-TURRAX® homogenizer IKA T10 at 11,500 rpm for 3 min at 50° C. in order to form an emulsion.

(ii) Microencapsulation

In a double-wall reactor, equipped with an IKA mechanical blade stirring system, preheated at 65° C., the previously prepared emulsion was introduced and stirred at a speed of 250 rpm. When the temperature of the emulsion had reached 65° C., the solution of m-xylenediamine (0.80 g, 5.88 mmol) in 5.0 g of a 2 wt % PVA solution was added drop by drop using a syringe under stirring at 248 rpm. The mixture was maintained stirred for five hours at 65° C. and then for 1 hour at 80° C. The total quantity of monomer used was 2.3 g. The amine was used in excess with respect to the acrylate monomer such as to have a molar ratio —NH/acrylate of 1.6. The weight ratio fragrance/water was 0.55.

FIG. 17 shows a photograph of these microcapsules.

Example 18: Preparation of Scented Microcapsules with a Coating of Cellule Fibers (i) Preparation of the Emulsion 22.0 g of fragrance were placed in a beaker, and the multi-acrylate monomer (dipentaerythritol penta-/hexa-acrylate mixture) (1.52 g, 2.90 mmol) was dispersed in the fragrance under magnetic stirring (350 rpm) at 50° C. Stirring was maintained until the solution became homogeneous. The fragrance/organic monomer assembly was progressively added to the aqueous solution of the surfactant prepared beforehand (40.0 g, PVA 2% by weight); the mixture was homogenized using an ULTRA-TURRAX® homogenizer IKA T10 at 11,500 rpm for 3 min at 50° C., in order to form an emulsion.

(ii) Microencapsulation

In a double-wall reactor, equipped with an IKA mechanical blade stirring system, preheated at 65° C., the previously prepared emulsion was introduced and stirred at a speed of 250 rpm. When the temperature of the emulsion had reached 65° C., the solution of m-xylenediamine (0.80 g, 5.88 mmol) in 5.0 g of a 2 wt % PVA solution was added drop by drop using a syringe under stirring at 250 rpm. The mixture was maintained stirred for five hours at 65° C. and then for 1 hour at 80° C. The total quantity of monomer used was 2.3 g. The amine was used in excess with respect to the acrylate monomer such as to have a molar ratio —NH/acrylate of 1.6. The weight ratio fragrance/water was 0.5.

(iii) Cellulose Coating 4 weight % of cellulose microfibers (Exilva F 01-L) were preheated at a temperature between 65° C. and 70° C. and introduced into the hot slurry under stirring. The hot mixture was homogenized for 30 minutes and then for two hours at room temperature. An adhesion test on cotton fiber was carried out: a cotton fiber was moistened and then immerged into the slurry. After strong and careful washing in water to simulate rinsing, the fiber was dried at room temperature.

FIG. 18 shows a photograph of a cotton fiber after immersion into the slurry solution followed by drying of the fiber, for microcapsules with a coated surface (picture (b)). This coating improves the adhesion of the microcapsules to the cotton fiber, compared to uncoated microcapsules (picture (a)).

The invention is not limited to the examples described and represented as diverse modifications can be brought thereto without departing from the scope of the invention.

What is claimed is:

1. A method for manufacturing microcapsules containing an active substance, the method comprising:
   providing an aqueous solution of a surfactant, an oily phase comprising said active substance and a first monomer, and a polar phase comprising a second monomer;
   preparing an oil-in-water emulsion by adding said oily phase to said aqueous solution of the surfactant;
   adding said polar phase to said oil-in-water emulsion to obtain a polymer by polymerization of said first monomer and said second monomer in a reaction mixture; and
   isolating said microcapsules, including a wall formed by said polymer and containing said active substance, from the reaction mixture;
   wherein said polymer is a poly(beta-amino ester).

2. The method according to claim 1, wherein said first monomer is a (multi)acrylate.

3. The method according to claim 2, wherein said first monomer is selected from the group consisting of:
   diacrylates;
   triacrylates;
   polymers carrying acrylic pendant functions;
   functional PBAE oligos; and
   mixtures thereof.

4. The method according to claim 1, wherein said second monomer is an amine.

5. The method according to claim 4, wherein said second monomer is selected from the group consisting of:
- primary amines of the type R—$NH_2$;
- primary diamines of the type $NH_2(CH_2)_nNH_2$, where n is between 1 and 20;
- primary diamines comprising an aromatic center;
- primary (multi)amines;
- secondary diamines; and
- polymers having primary and/or secondary amine functions.

6. The method according to claim 1, wherein said polymerization comprises stirring at a temperature of from 20° C. to 100° C.

7. The method according to claim 1, wherein said surfactant is a macromolecular surfactant.

8. The method according to claim 1, wherein said active substance is selected from the group consisting of:
- essential oils and fragrances;
- inks, paints, thermochromic and/or photochromic substances, dyes, and glues, biocidal effect products, fungicidal effect products, antiviral effect products, phytosanitary effect products, cosmetic effect products, pharmaceutical active ingredients; and
- natural and edible oils, vegetable and edible oils, liquid alkanes, esters and fatty acids.

9. The method according to claim 1, wherein a shell of said microcapsules is modified by adding a polymeric coating deposited onto a surface of said microcapsules, or by adding a radical initiator to at least one of the aqueous and the oily phase, or by adding to the aqueous phase a water soluble acrylate capable of modifying a surface state of said microcapsules.

10. The method according to claim 2, wherein the (multi) acrylate is a (multi)acrylate of formula X'—(—O(C=O)—CH=$CH_2)_n$, n≥4, and where X' represents a molecule whereon n acrylate units are grafted.

11. The method according to claim 3, wherein the triacrylates are selected from the group consisting of trimethylol propane triacrylate, tetraacrylates, pentaacrylates, hexaacrylates, and mixtures between these different acrylates of the type $O[CH_2C(CH_2OR)_3]_2$ where R is H or COCH=$CH_2$.

12. The method according to claim 3, wherein the functional PBAE oligos are prepared by reaction of diacrylate compounds with a functional primary amine and/or a functional secondary diamine.

13. The method according to claim 4, wherein the second monomer is selected from the group consisting of meta-xylylene diamine, tris(2-aminoethyl)amine, tetraethylene pentamine, piperazine, and polyethyleneimine.

14. The method according to claim 7, wherein the macromolecular surfactant is selected from the group consisting of polyacrylates, methylcelluloses, carboxymethylcelluloses, polyvinyl alcohol, partially etherified polyvinyl alcohol, partially esterified polyvinyl alcohol, polyacrylamide, synthetic polymers having anhydride functions or carboxylic acid, and ethylene/maleic anhydride copolymers.

* * * * *